United States Patent [19]

Sabanayagam et al.

[11] Patent Number: 5,453,162
[45] Date of Patent: Sep. 26, 1995

[54] METHOD AND APPARATUS FOR GEL ELECTROPHORESIS USING TWO ELECTRIC FIELDS

[75] Inventors: Chandran R. Sabanayagam, Chadds Ford, Pa.; George M. Holzwarth, Winston-Salem; Eric H. Lai, Chapel Hill, both of N.C.

[73] Assignees: University of North Carolina at Chapel Hill, Raleigh; Wake Forest University, Winston-Salem, both of N.C.

[21] Appl. No.: 119,033

[22] Filed: Sep. 9, 1993

[51] Int. Cl.$^6$ .................................................. B01D 57/02
[52] U.S. Cl. ................................... 204/180.1; 204/182.8
[58] Field of Search ........................ 204/182.8, 180.1

[56] References Cited

U.S. PATENT DOCUMENTS

| | | | |
|---|---|---|---|
| 4,148,703 | 4/1979 | Trop et al. | 204/182.8 |
| 4,473,452 | 9/1984 | Cantor et al. | 204/180 G |
| 4,737,251 | 4/1988 | Carle et al. | 204/182.8 |
| 4,740,283 | 4/1988 | Laas et al. | 204/182.8 |
| 4,900,416 | 2/1990 | Makino et al. | 204/182.8 |
| 4,971,671 | 11/1990 | Slater et al. | 204/180.1 |
| 5,011,586 | 4/1991 | Finney et al. | 204/182.8 |
| 5,028,308 | 7/1991 | Beritashvili et al. | 204/182.8 |
| 5,059,294 | 10/1991 | Lizardi | 204/182.8 |
| 5,108,567 | 4/1992 | Kölble | 204/180.1 |
| 5,126,022 | 6/1992 | Soane et al. | 204/182.8 |
| 5,167,784 | 12/1992 | Noolandi | 204/182.8 |
| 5,167,790 | 12/1992 | Carle et al. | 204/299 R |
| 5,176,805 | 1/1993 | Tombs | 204/182.8 |

OTHER PUBLICATIONS

C. Turmel, et al., *High–resolution Zero Integrated Field Electrophoresis of DNA, Electrophoresis of Large DNS Molecules: Theory and Applications* 101–131 (1990).

B. W. Birren et al., *Optimized conditions for pulsed field gel electrophoretic separations of DNA Nucleic Acids Research*, 16, 7563–7582 (1988).

G. F. Carle, et al., *Electrophoretic Separations of Large DNA Molecules by Periodic Inversion of the Electric Field Science* 232, 65–67 (1986).

Primary Examiner—Kathryn Gorgos
Assistant Examiner—C. Delacroix-Muirheid
Attorney, Agent, or Firm—Bell, Seltzer, Park & Gibson

[57] ABSTRACT

Disclosed is a method and apparatus for gel electrophoresis which simultaneously employs two or more electric fields in a single gel. According to this invention, which is defined as Multiple-Zone Pulsed-Field Gel Electrophoresis (MZPFGE), the electric field is set to different values in two or more spatially distinct regions of the gel. The difference in values may be related to time dependence, field amplitude or both.

9 Claims, 7 Drawing Sheets

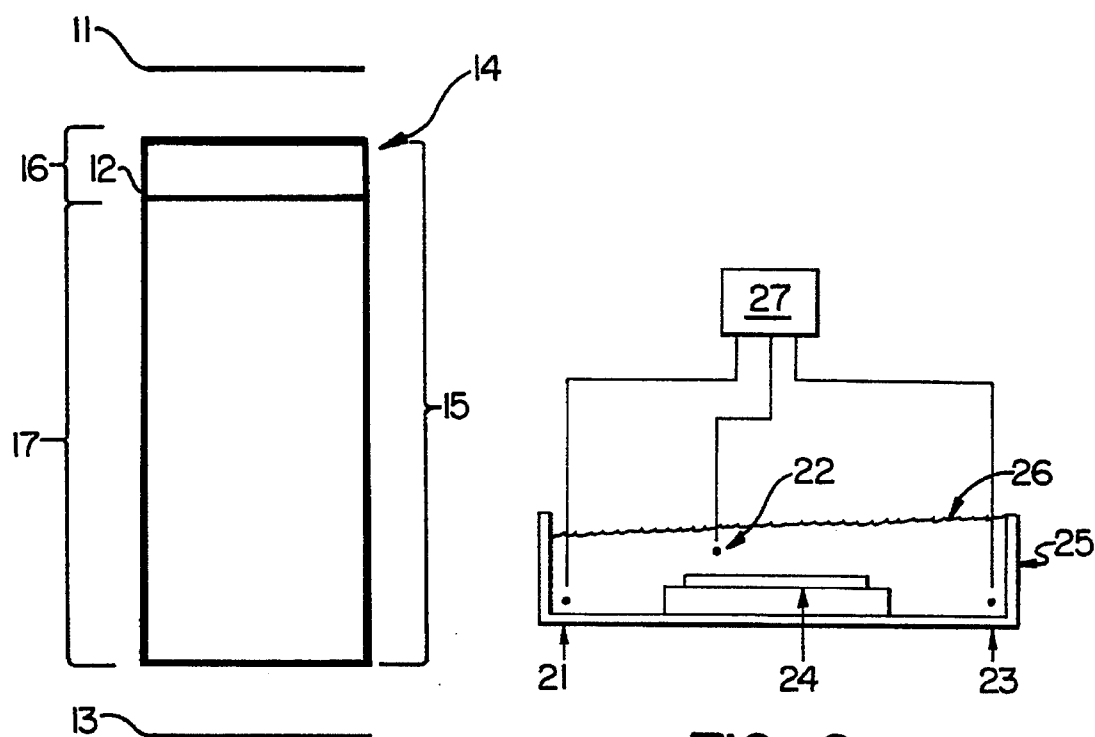
FIG. 1.
FIG. 2.
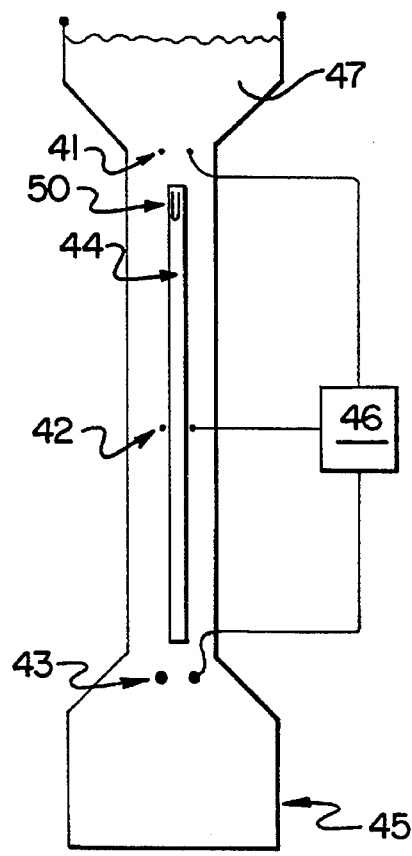
FIG. 3.

METHOD AND APPARATUS FOR GEL ELECTROPHORESIS USING TWO ELECTRIC FIELDS

This invention was made with Government support under grant number DMB 8906213 and BIR 9016214 from the National Science Foundation, and grant number R55-HG00707-01 from the National Institutes of Health. The Government has certain rights to this invention.

FIELD OF THE INVENTION

This invention relates to a method of gel electrophoresis, termed multiple-zone pulsed-field gel electrophoresis (MZPFGE), where two or more different electric fields are applied to the gel at the same time but in distinct spatial regions of the gel.

BACKGROUND OF THE INVENTION

Electrophoresis involves the separation of mixtures of molecules by differential migration of the molecules through a transport medium in an electric field. Many particles in an aqueous medium acquire an electrical charge due to ionization and thus move in response to an external electrical field. During electrophoresis a mixture of macromolecules is eventually separated into a series of distinct bands in order of charge density or size. Once the bands of molecules are separated they can be identified by suitable means such as staining and optical scanning. Electrophoresis in a gel medium is an important method of separating proteins, nucleic acids, and other macromolecules in mixture.

A given electric field may be altered by changing either or both of two parameters: (1) the voltage gradient, or intensity of the electric field; or (2) the direction, or orientation of the electric field. In conventional gel electrophoresis, at any given time a single electric field is applied to the gel, i.e., the intensity and orientation of the electric field being applied to the gel is constant in time throughout the electrophoretic separation.

In electrophoretic methods for separating large double stranded DNA molecules, several techniques have been advanced to increase the band resolution (i.e., increase the distance between bands without a corresponding increase in the width of the bands, or decrease the width of the bands without a corresponding decrease in the distance between bands). The advantages of pulsing the electric field (i.e., periodically changing the field orientation) during gel electrophoresis of high molecular weight double-stranded DNA was first demonstrated by Schwartz and Cantor. Schwartz et al., *Cold Spring Harbor Symp. Quant. Biol.* 47, 189 (1983); Schwartz and Cantor, *Cell* 37, 67 (1984); Cantor and Schwartz U.S. Pat. No. 4,473,452; Gardiner et al., *Somatic Cell Mol. Genet.*, 12, 185 (1986).

A number of variants of pulsed-field gel electrophoresis (PFGE) have been described in the literature and are commercially available. In field-inversion gel electrophoresis (FIGE) the electric field alternates in polarity, and the durations of the "forward" and "back" pulses (the pulse amplitudes) are chosen to achieve a particular separation; net migration is achieved by using a longer time or higher voltage in one direction than in the other. U.S. Pat. No. 4,737,252; Carle et al., *Science*, 232, 65 (1986). In contour-clamped, homogeneous field electrophoresis (CHEF), the field direction is changed by 120° while the field amplitude remains constant. Chu et al., *Science* 234, 1582 (1986). In rotating-gel electrophoresis, the field direction is changed by rotating the gel itself. Southern et al., *Nucl. Acids. Res.* 15, 5925 (1987). In transverse alternating field electrophoresis (TAFE), the field alternates in two directions approximately transverse to the plane of the gel. Gardiner et al., *Somatic Cell and Molecular Genetics*, 12, 185 (1986); U.S. Pat. No. 4,473,452. In programmable, autonomously controlled electrophoresis (PACE), the potentials of 24 electrodes are set independently, permitting exploration of a diversity of field directions and amplitudes. Birren et al., *Nucl. Acids Res.*, 15, 7563 (1988). Pulsed fields have also been used to improve the separation of single-stranded DNAs. Birren et al., *Nucl. Acids. Res.* 18, 1481 (1990); Ulanovsky et al., *Nature* 343, 190 (1990).

Several variants of field inversion gel electrophoresis (FIGE) have been described. In their original description of FIGE, Carle et al. presented separation data for identical field amplitudes, $E_+ = E_-$, but different forward and back pulse durations, $t_+ \neq t_-$ (where $E_+$ indicates an electric field causing a molecule to move away from its starting point in a gel, $E_-$ indicates an electric field causing a molecule to move toward its starting point in a gel, $t_+$ indicates the duration of a single pulse in field $E_+$ and $t_-$ indicates the duration of a single pulse in field $E_-$). Carle et al. noted that resolution in a particular size range could also be achieved if $t_+ = t_-$ but $E_+ \neq E_-$. Carle et al., *Science*, 232, 65 (1986). Somewhat better separations are possible if different durations are used for $t_+$ and $t_-$, and different amplitudes are used for $E_+$ and $E_-$; this method has been termed Asymmetric Voltage Field-Inversion Gel Electrophoresis (AVFIGE). Birren et al., *Nucl. Acids. Res.* 18, 1481 (1990); Denko et al., *Analyt. Biochem.* 178, 172 (1989). A variant of AVFIGE, called Zero Integrated Field Electrophoresis (ZIFE) has been explored by Noolandi and Turmel. Turmel et al., in *Electrophoresis of Large DNA Molecules,* Birren and Lai (Eds.), Cold Spring Harbor Press, 101–132 (1990); Noolandi and Turmel, Pulsed Field Gel Electrophoresis, in *Methods in Molecular Biology,* vol. 12, p. 73, Burmeister and Ulanovsky (Eds.), Humana Press (1992). In ZIFE, both the pulse times and the pulse amplitudes are varied during a run, while in principle maintaining the product $(E_+ t_+)$ equal to $(E_- t_-)$. With this condition, $\int E dt = 0$ over an integral number of cycles.

A common feature of pulsed-field gel electrophoresis (PFGE) and its variants is that the time-dependence is the same in all areas of the gel. At any given time a single set of parameters defines the electric field being applied to the gel, although those parameters may change during the course of the electrophoretic separation. In contrast, in MZPFGE, multiple distinct electric fields are created within the gel, with distinct spatial regions of the gel subjected to different fields at the same time.

SUMMARY OF THE INVENTION

A first aspect of the present invention is a method for conducting gel electrophoresis in which at least two electric fields are applied to an electrophoretic gel, so that at least two distinct zones having different electric field values exist simultaneously in the gel. This method is termed multiple-zone pulsed-field gel electrophoresis (MZPFGE).

A further aspect of the present invention are apparatus for conducting multiple-zone pulsed-field gel electrophoresis.

The foregoing and other objects and aspects of the present invention are explained in detail in the drawings herein and the specification set forth below.

BRIEF DESCRIPTION OF THE DRAWINGS

FIG. 1 is a schematic diagram of an apparatus for carrying out the multiple-zone pulsed-field gel electrophoresis (MZPFGE) method.

FIG. 2 is a schematic diagram of a horizontal gel electrophoresis apparatus designed to use the multiple-zone pulsed-field gel electrophoresis (MZPFGE) method.

FIG. 3 is a schematic diagram of a vertical gel electrophoresis apparatus designed to use the multiple-zone pulsed-field gel electrophoresis (MZPFGE) method.

DETAILED DESCRIPTION OF THE INVENTION

Figure 4:
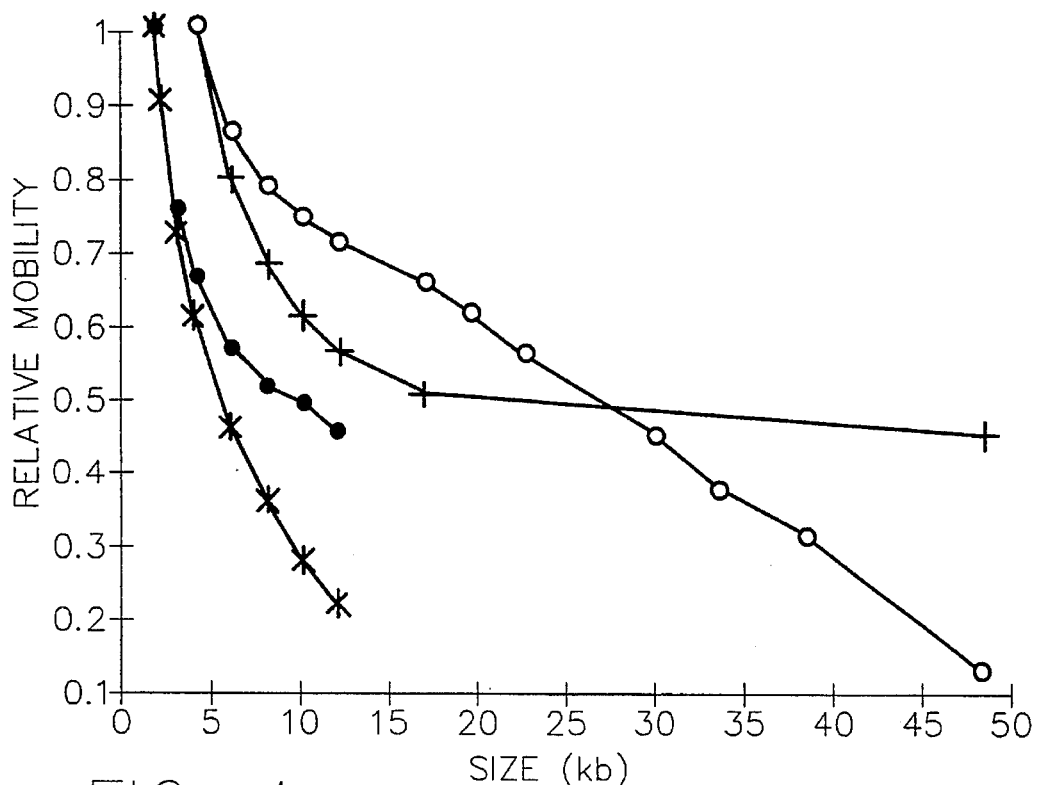
FIG. 4 is a graph comparing the relative mobility of double stranded DNA fragments separated with conventional electrophoresis and with MZPFGE in a horizontal apparatus. Conventional electrophoresis gel experiments were carried out at constant field-strengths of 6 V/cm (1–12 kb separation=closed circles; 1–50 kb separation=plus signs). The MZPFGE gel experiments were carried out with the following conditions. MZPFGE 1–50 kb (open circles): In Zone I, sample placed 4 cm from interface, $E_+$ was 12 V/cm, $t_+$ was 0.3 seconds, $E_-$ was 6 V/cm, $t_-$ was 0.3 seconds; In Zone II a constant field strength of 7 V/cm was applied. In MZPFGE 1–12 kb (asterisks): In Zone I, sample placed 4 cm from interface, $E_+$ was 6 V/cm, $t_+$ was 0.1 s, $E_-$ was 3.2 V/cm, $t_-$ was 0.1 s; In Zone II a constant field strength of 3.2 V/cm was applied.

A first aspect of the present invention is a method for conducting gel electrophoresis, called multiple-zone pulsed-field gel electrophoresis (MZPFGE). In the present invention two or more electric fields are applied to a gel at any given time, such that two or more spatially distinct zones are created in the gel, each zone subjected to a distinct electric field. The difference in the electric field parameters can be in their time-dependence (periodicity) or field amplitudes, or both. Four advantages of such a method are (1) molecules move from the sample well to an equilibrium position; (2) the bands become sharp as forces act in opposite directions on the leading and trailing edges of a band at equilibrium, (3) the length of a gel can be used to display either a narrow or broad window of separation range (depending on the steepness of the gradient in time-dependence or field strength) and (4) the fields can be tailored to provide an essentially linear dependence of mobility on DNA size.

An embodiment of the present invention utilizes 3 electrodes or electrode pairs to create two electrophoretic zones in a single gel. Standard horizontal or vertical gel electrophoresis chambers may be utilized. One electrode (or electrode pair) is placed at each end of a gel contained within a chamber, and a third electrode (or electrode pair) is placed at a point somewhere intermediate the other two electrodes (or electrode pairs). A schematic diagram of an embodiment of the present invention is shown in FIG. 1, where electrode B (12) is placed intermediate electrodes A (11) and C (13). Sample wells (14) are located in the gel (15), intermediate electrode A (11) and B (12). Zone I (16) is the region of gel between electrode A (11) and electrode B (12), while Zone II (17) is the region of gel between electrode B (12) and electrode C (13). Power supply means (not shown) are operatively connected to electrodes A, B, and C for applying a voltage across the gel. The potential difference $V_A$–$V_B$ fixes $E_+$, $E_-$, $t_+$ and $t_-$ in Zone I, while $V_B$–$V_C$ fixes $E_+$, $E_-$, $t_+$ and $t_-$ in Zone II, where $E_+$ indicates an electric field causing a molecule to move away from its starting point in a gel, $E_-$ indicates an electric field causing a molecule to move toward its starting point in a gel, $t_+$ indicates the duration of a single pulse in field $E_+$, and $t_-$ indicates the duration of a single pulse in field $E_-$.

The present invention may be embodied in either horizontally or vertically configured gel electrophoresis apparatus. In one embodiment of the present invention, the MZPFGE method is conducted in a horizontal gel electrophoresis apparatus, such as that diagrammed in FIG. 2. The apparatus of FIG. 2 comprises a standard submarine gel electrophoresis chamber (25), a first electrode A (21) and a second electrode C (23). To this standard apparatus is added a third electrode, electrode B (22), which is placed in the buffer (26) above the gel (24) and intermediate the other two electrodes. Power supply means (27) generate the electric fields.

In another embodiment of the present invention, the MZPFGE method is conducted in a vertical gel electrophoresis apparatus, such as that diagrammed in FIG. 3. The apparatus of FIG. 3 comprises a vertical gel electrophoresis chamber (45), a first electrode pair A (41) placed in the buffer above the gel (44) and a second electrode pair C (43) placed in the buffer (47) below the gel (44). Sample wells (50) are located near the top of the gel. A third electrode pair B (42) is placed in the gel chamber, intermediate electrode pairs A and C and below the sample wells, with the gel (44) sandwiched between the two electrodes. Power supply means (46) generate the electric fields.

It will be readily apparent to those of ordinary skill in the art that many power supply arrangements are suitable means for generating the electric fields required in MZPFGE. Any arrangement suitable for electrophoresis and capable of generating the desired parameters can be used. Where a pulsed field is used, power supply means must be capable of generating electric fields of opposing directions, and of switching between the fields so generated. See, e.g., Gardiner et al., *Som. Cell Molec. Genet.*, 12, 185 (1986).

One preferred embodiment of the power supply means comprises two separate power supply units connected to a high voltage switching unit which is connected to electrodes A and B, while a third power supply is connected to electrodes B and C. A more preferred embodiment comprises two commercial programmable bipolar operational power supplies (BOPS). One BOPS is connected to electrode pairs A and B, the other to electrode pairs B and C. The system is controlled using a computer. A preferred arrangement comprises a digital computer equipped with an IEEE-488 Board and an IEEE-488 to analog converter (Kepco SN 488–122), which controls a Kepco Bipolar Operational Power Supply (BOP) (Kepco BOP 500-M)(Kepco Inc., Flushing, N.Y.).

Using the present invention, the mobility of DNA molecules of a given size will differ in Zones I and II of the gel. The values of the field strengths and pulse durations in the two zones of the present invention can be selected such that (1) distance between bands is increased, (2) widths of bands are decreased, (3) the interface between the two zones acts as a gate which allows only molecules smaller than a preselected size to advance into Zone II, or (4) the interface between the two zones acts as a gate which allows molecules of preselected increasing sizes to advance into Zone II.

The present invention can increase the resolution of electrophoretic separations. The resolution of any gel separation depends on both (1) the distance between the bands and (2) the widths of the individual bands. By using field values that selectively retard the larger molecules in the sample in Zone 1, the present invention increases the distance between the sample bands over that obtainable using previously known techniques.

In a preferred embodiment of the present invention an AVFIGE field is present in Zone I of the electrophoretic gel. The values of the AVFIGE field are selected based on the size of the molecules in the sample to be separated. Most preferably, the values are selected so that the larger molecules in the sample are selectively retarded in Zone I while the smaller molecules migrate into Zone II. In this way the DNA molecules of a sample are slowly released from Zone I to Zone II according to molecule size, due to the pulsed field conditions in Zone I. Either a constant field or a pulsed field can be used in Zone II. As the DNA molecules migrate into Zone II, they will be separated according to the electrophoretic conditions in that zone.

The individual bands in a gel separation may be sharpened (i.e., compressed) using the present invention. This can be accomplished if the voltage gradient of the forward electric field in Zone I is higher than that of the field in Zone II, or if the periodicity of the field (the time-dependence) causes the sample molecules to move forward more rapidly in Zone I than in Zone II. Under these conditions, as the molecules migrate from Zone I to Zone II the leading side of the band slows down while the trailing side of the band is forced ahead. This serves to compress the band and thereby decrease its width.

In another embodiment of the present invention the interface between the two zones allows only molecules smaller than a pre-selected size to advance into Zone II. The values of the field in Zone I are selected so that the velocity of molecules larger than a preselected size is negative, while the velocity of smaller molecules is positive. Most preferably, a pulsed field is present in both Zones I and II, where the field in Zone I ($E_I$) is zero whenever the field in Zone II ($E_{II}$) is negative. Under such conditions the interface acts as a "gate" and allows only molecules of a preselected size to migrate into Zone II. By altering the values of the electric field in Zone I, the threshold molecular size permitted to migrate into Zone II can be altered over the duration of the electrophoretic separation, and the interface gate will allow molecules of different threshold sizes to advance into Zone II.

In using apparatus embodying the present invention, the electric field parameters are adjusted in a manner specific for the molecules in the sample to be separated and for the separation desired. The value of $E_+$ and $E_-$ may range from 0 to about 1,000 V/cm; the values of $t_+$ and $t_-$ may range from about 0.001 second to about 10,000 seconds.

The present invention can be conducted using power supplies, electrodes, gel media, electrophoresis chambers, and other elements as found in known devices, combined as taught herein. See, e.g., Monthony et al. U.S. Pat. Nos. 3,948,743; Delony et al. U.S. Pat. No. 4,574,040; Cantor et al. U.S. Pat. No. 4,861,448; Hochstrasser U.S. Pat. No. 4,874,490; Kushner et al. U.S. Pat. No. 4,954,236; Fernwood et al. U.S. Pat. No. 4,994,166; Chu et al. U.S. Pat. No. 5,073,246; (applicants specifically intend that the disclosure of all U.S. patent references cited herein be incorporated herein in their entirety).

It will be apparent to one skilled in the art that the physical and electrical parameters of the present invention may be varied considerably to achieve desired separations without departing from the spirit of the invention. It will also be readily apparent to one skilled in the art that the present invention can be utilized to analyze different types of molecules, including but not limited to, double-stranded DNA, single-stranded DNA, RNA, oligonucleotides, proteins and polypeptides. The present invention can be utilized to separate complex mixtures of DNA such as the chromosomes of yeast or restriction fragment digests of chromosomal DNA, including that of humans. Thus it is also apparent that the present invention can be utilized in any situation in which large DNA molecules must be separated by size for the purpose of sequencing.

The principles of the present invention may be embodied in electrophoresis cells designed for electrophoresis gels arranged horizontally or vertically. Such cells are easily fabricated or modified from those available commercially. It will be readily apparent to one skilled in the art that the present invention is not limited to the specific illustrative equipment disclosed herein. The gel utilized may be of any suitable geometry, including but not limited to slab, strip, tube, and gel-filled capillary. Any gel suitable for electrophoresis may be used in the present invention, including but not limited to polyacrylamide, starch, agar, agarose and the like.

The present invention is explained in greater detail in the following examples, where mm means millimeter, cm means centimeter, hr means hour, s means second, V means volt, TBE means tris(hydroxymethyl) aminomethane-disodium ethylenediaminetetraacetate-boric acid buffer, kb means kilobase pair, DS means double-stranded, SS means single-stranded, MZPFGE means multiple-zone pulsed-field gel electrophoresis, MZPFGE interface means the boundary between the zones of the electrophoretic gel; PFGE means pulsed field gel electrophoresis, ZIFE means zero integrated field electrophoresis, ZIVE means zero integrated velocity electrophoresis, ° C. means degrees centigrade, M means molecular weight, $\Delta x$ means displacement, $\Delta t$ means time difference, $E_+$ indicates an electric field causing a molecule to move away from its starting point in a gel, $E_-$ indicates an electric field causing a molecule to move toward its starting point in a gel, $t_+$ indicates the duration of a single pulse in field $E_+$, $t_-$ indicates the duration of a single pulse in field $E_-$, $E_I$ indicates the electric field in Zone I of an MZPFGE gel, indicates the electric field in Zone II of an MZPFGE gel.

EXAMPLE 1

Band Separation Using MZPFGE

Gel separations achieved with conventional electrophoresis were compared with those achieved using MZPFGE. Conditions of the two electrophoretic methods were kept as similar as possible. Conventional constant field-strength experiments were carried out at 6 V/cm. MZPFGE gel experiments were carried out with the following conditions: MZPFGE 1–50 kb: In Zone I, sample placed 4 cm from interface, $E_+$=12 V/cm, $t_+$=0.3 s, $E_-$=6 V/cm, and $t_-$= 0.3 s; In Zone II, constant field strength of 7 V/cm. MZPFGE 1–12 kb: In Zone I, sample placed 4 cm from interface, $E_+$=6 V/cm, $E_-$=3.2 V/cm; In Zone II, constant field strength of 3.2 V/cm.

Results are shown in FIG. 4; note the near-linear shape of the migration vs. molecular weight curves. These results show that the logarithmic dependence of DS DNA separation in agarose gels is transformed into a linear function using MZPFGE. This transformation is crucial to the separation of small DS DNA and of SS DNA molecules. Preliminary experiments show that the distances between bands of DS DNA in the size range 1–50 kb can be increased by as much as 5-fold with MZPFGE as compared to conventional electrophoresis (FIG. 4).

EXAMPLE 2

Calculation of Migration Distances in MZPFGE

The migration distances of large (>50 kb) DS DNA fragments in MZPFGE were calculated using mobility data of DNA under conventional and ZIFE conditions. Mobility data is also available from published sources. See, e.g., Turmel et al., in *Electrophoresis of Large DNA Molecules*, Birren and Lai (Eds.), Cold Spring Harbor Press, 101–132 (1990). The mobility of DS DNA molecules from 22–460 kb under conventional and ZIFE conditions are shown in Table 1.

All electrophoresis experiments were carried out in 1% LE agarose in 0.5×TBE at 14° C. A horizontal electrophoresis apparatus as shown in FIG. 2 was used. The ZIFE gels were run with $E_+$=2.84 V/cm, $t_+$=15 s, $E_-$=0.84 V/cm, and $t_-$=21 s (ZIFE I); or $E_+$=2.84 V/cm, $t_+$=40 s, $E_-$=0.84 V/cm, and $t_-$=56 s (ZIFE II). The reverse switching times were 1.4 times the forward times. The run duration of the ZIFE gels was 65 hr. The conventional gel was performed at 6 V/cm for 12 hr.

TABLE 1

| | Mobility of DS DNA (22–460 kb) | | |
|---|---|---|---|
| Size (kb) | ZIFE I (15 s) (cm/hr) | ZIFE II (40 s) (cm/hr) | Conventional (non-pulsing) (cm/hr) |
| 22 | .15 | .17 | 0.6 |
| 48.5 | .14 | .15 | 0.6 |
| 110 | .11 | .14 | 0.6 |
| 210 | .04 | .12 | 0.6 |
| 290 | .02 | 0.1 | 0.6 |
| 360 | .02 | .08 | 0.6 |
| 460 | .02 | .03 | 0.6 |

Using this mobility data, the distance traveled by various DNA sizes at different MZPFGE run durations can be calculated and predicted. As an example, for a 22 kb fragment after a 35 hour MZPFGE gel run, where the distance between the sample wells and the interface is 1.5 cm, conditions in Zone I match the ZIFE I conditions of Table 1, and conditions in Zone II match the conventional non-pulsing conditions of Table 1, it will take the 22 kb molecule approximately 10 hours to move from Zone 1 into Zone II (1.5 cm/0.15 cm per hr=10 hr). The 22 kb molecule will then migrate in Zone II at a velocity of 0.6 cm/hr (conventional non-pulsing gel) for an additional 25 hrs. After 35 hours, the distance traveled by the 22 kb molecule in this gel will be equal to: (distance between sample and interface)+(total time—Zone I time)(Zone II velocity), or:

$$.5 \text{ cm} + (35 \text{ hr} - 10 \text{ hr})(.6 \text{ cm/hr}) = .5 \text{ cm}.$$

We have calculated the distances that are traveled by double stranded DNA molecules from 22–460 kb under six conditions: two ZIFE, two 120° PFGE, and two MZPFGE, as shown in Table 2. The running conditions of the 120° 2-field PFGE gels are chosen to yield maximum resolution in the same size range as the ZIFE gels.

The distances traveled by the DNA fragments in MZPFGE gels are calculated according to the following assumptions: (1) the distance between sample starting point and interface is 1.5 cm, and (2) the conditions in Zone I of MZPFGE I and MZPFGE II gels are the same, respectively, as the conditions of the ZIFE I and ZIFE II gels of Table 1.

Note that these calculations confirm that MZPFGE can greatly expand the distances between bands and increase the speed of electrophoretic separations as compared to conventional pulsed field gels.

TABLE 2

Calculated Distance Traveled (cm) by Double Stranded DNA Molecules in ZIFE, 120° PFG and MZPFGE Gels

| Size (kb) | ZIFE I | 120° PFGE I | MZPFGE I | ZIFE II | 120° PFGE II | MZPFGE II |
|---|---|---|---|---|---|---|
| 22 | 9.0 | 12.3 | 16.5 | 9 | 17.5 | 26.2 |
| 48.5 | 8.4 | 10.9 | 16.1 | 8 | 15.5 | 25.5 |
| 110 | 6.6 | 9.5 | 14.3 | 7.4 | 14.3 | 25 |
| 210 | 2.4 | 5.3 | 1.4 | 6.4 | 12 | 24 |
| 290 | 1.2 | 3 | 0.7 | 5.3 | 8.5 | 22.5 |
| 360 | 1.2 | 3 | 0.7 | 4.3 | 7 | 20.3 |
| 460 | 1.2 | 3 | 0.7 | 1.6 | 4.5 | 1.5 |

The running conditions of the gels are as follows:

ZIFE I $E_+=2.84$ V/cm, $t_+=15$ s, $E_-=0.84$ V/cm, and $t_-=21$ s, 60 hour run;

ZIFE II $E_+=2.84$ V/cm, $t_+=40$ s, $E_-=0.84$ V/cm, and $t_-=56$ s, 54 hour run;

120° PFGE I E=6 V/cm, 15 s pulse duration, 35 hr run;

120° PFGE II E=6 V/cm, 30 s pulse duration, 50 hr run;

MZPFGE I Samples placed 1.5 cm from interface, $E_+=2.84$ V/cm, $t_+=15$ s, $E_-=0.84$ V/cm, and $t_-=21$ s; Zone II: 6 V/cm; 35 hour run time; and MZPFGE II Samples placed 1.5 cm from interface, $E_+=2.84$ V/cm, $t_+=40$ s, $E_-=0.84$ V/cm, and $t_-=56$ s; Zone II: 6 V/cm; 50 hour run time.

EXAMPLE 3

Separation of Double-Stranded DNA

Separation Between 100–200 kb. Using the ZIFE I conditions as described in Example 2, the distance between 110 and 210 kb fragments of DS DNA is 4.2 cm after 60 hours (Table 2). The best separation that can be obtained in a 120° 2-field PFGE gel, as described above, is also approximately 4.2 cm after 35 hr (Table 2). Using the MZPFGE I condition described in Table 2, the distance between 110 and 210 kb fragments is 12.9 cm after 35 hr (Table 2). This is a 3-fold increase in separation distance over ZIFE and 120° PFGE.

Another advantage of MZPFGE is the increased migration of smaller DNA fragments without the loss of resolution. For example, the 22 kb fragment migrates approximately 25% faster in MZPFGE than in 120° PFG (see Table 2).

Separation Between 360–460 kb. Larger molecules can be retarded in Zone I by ZIFE conditions more readily than smaller molecules, as shown by the figures of Table 2. After about 50 hours, the maximum distance between 360 and 460 kb fragments obtained with optimum ZIFE and 120° PFG gels are 2.7 and 2.5 cm, respectively. Using MZPFGE, a separation distance of 18.8 cm can be achieved with the same run duration. This is a 7-fold increase in separation distance. According to calculations as shown in Table 2, a 100 kb size difference spread among 18.8 cm, or approximately 5 kb/cm, should be achievable. This translates into approximately 1 kb resolution in the 350 kb to 450 kb range. This resolution will be useful for separating yeast artificial chromosomes from natural yeast chromosomes. This degree of separation obtained with the MZPFGE technique is due to the fact that after 50 hours, the 460 kb fragment is still in Zone I while the 360 kb fragment is migrating rapidly in Zone II.

EXAMPLE 4

MZPFGE and Single-Stranded DNA Separation

The mobilities of single-stranded DNA molecules from 50–750 bases under conventional and asymmetric voltage field inversion gel electrophoresis (AVFIGE) are shown in Table 3. These mobilities are actual data taken from gel runs using a horizontal gel electrophoresis apparatus (as diagrammed in FIG. 2). Using this mobility data, the distance traveled by various SS DNA sizes at different run durations can be calculated.

TABLE 3

Mobility of SS DNA in Conventional and AVFIGE Gels

| Size (bases) | Conventional (cm/hr) | AVGFI (cm/hr) |
|---|---|---|
| 50 | 12.2 | 1.2 |
| 100 | 9.38 | 0.87 |
| 200 | 5.51 | 0.50 |
| 300 | 3.76 | 0.33 |
| 400 | 2.76 | 0.24 |
| 500 | 2.25 | 0.17 |
| 600 | 1.87 | 0.12 |
| 750 | 1.60 | 0.07 |

Gels were 80 cm in length, 5% polyacrylamide gels. The voltage gradient of the conventional gel was 35 V/cm. The AVFIGE condition used was $E_+=12.5$ V/cm, $t_+=1$ s, $E_-=35$ V/cm, and $t_-=0.25$ s.

The following example illustrates how to calculate the distance traveled by 50 base DNA molecules after a 10 hour MZPFGE run using the conditions as described in Table 3 (AVFIGE conditions in Zone I; conventional gel in Zone II). If the distance between the samples and the interface is 2 cm, it will take the 50 base DNA molecule approximately 1.67 hours to move from Zone I into Zone II (2 cm/1.2 cm per hr=1.67 hr). The 50-base molecule will then migrate in Zone II at a velocity of 12.2 cm/hr for an additional 8.33 hrs. After 10 hours, the distance traveled by the 50 base molecule in this MZPFGE gel will be equal to: (distance between sample and interface)+(total run time−run time in zone I)(velocity in Zone II):

$$2 \text{ cm}+(10 \text{ hr} -.67 \text{ hr}) (.2 \text{ cm/hr})=102 \text{ cm}.$$

The distance traveled by the same molecule in a conventional sequencing gel (35 V/cm):

$$10 \text{ hr} \times .2 \text{ cm/hr}=122 \text{ cm}.$$

The distances traveled by single-stranded DNA molecules from 50–750 bases after 10, 20, and 28 hour run times have been calculated (Table 4). Both gels are 72 cm long, 5% polyacrylamide gels. The voltage gradient of the conventional gel is 35 V/cm. For the MZPFGE gel, the distance between the sample wells and the interface is 2 cm; the AVFIGE condition in Zone I is $E_+=12.5$ V/cm, $t_+=1$ s, $E_-=35$ V/cm, and $t_-=0.25$ s; conventional electrophoresis (35 V/cm) is used in Zone II.

The calculations of Table 4 predict that the distances between bands in MZPFGE can be greatly expanded as compared to those in conventional sequencing gels. The larger DNA molecules are preferentially affected because of the AVFIGE conditions in Zone I. A 3-fold increase in separation distance between the 600 and the 750 base molecules is predicted after a 28 hour run time (20 cm in MZPFGE vs 7 cm in a conventional gel).

TABLE 4

Calculated Distance Traveled by SS DNA Molecules in Conventional and MZPFGE Gels After Various Run Times

| Size (bases) | 10 hr | | 20 hr | | 28 hr | |
|---|---|---|---|---|---|---|
| | Conventional (cm) | MZPFGE (cm) | Conventional (cm) | MZPFGE (cm) | Conventional (cm) | MZPFG (cm) |
| 50 | 122 | 102 | 244 | 224 | 342 | 321 |
| 100 | 94 | 72 | 188 | 166 | 263 | 241 |
| 200 | 55 | 33 | 110 | 88 | 154 | 132 |
| 300 | 38 | 15 | 76 | 52 | 105 | 82 |
| 400 | 18 | 4.3 | 56 | 32 | 77 | 54 |
| 500 | 23 | 1.7 | 46 | 19 | 63 | 37 |
| 600 | 19 | 1.2 | 38 | 6.2 | 52 | 22 |
| 750 | 16 | 0.7 | 32 | 1.4 | 45 | 2 |

Figure 5:
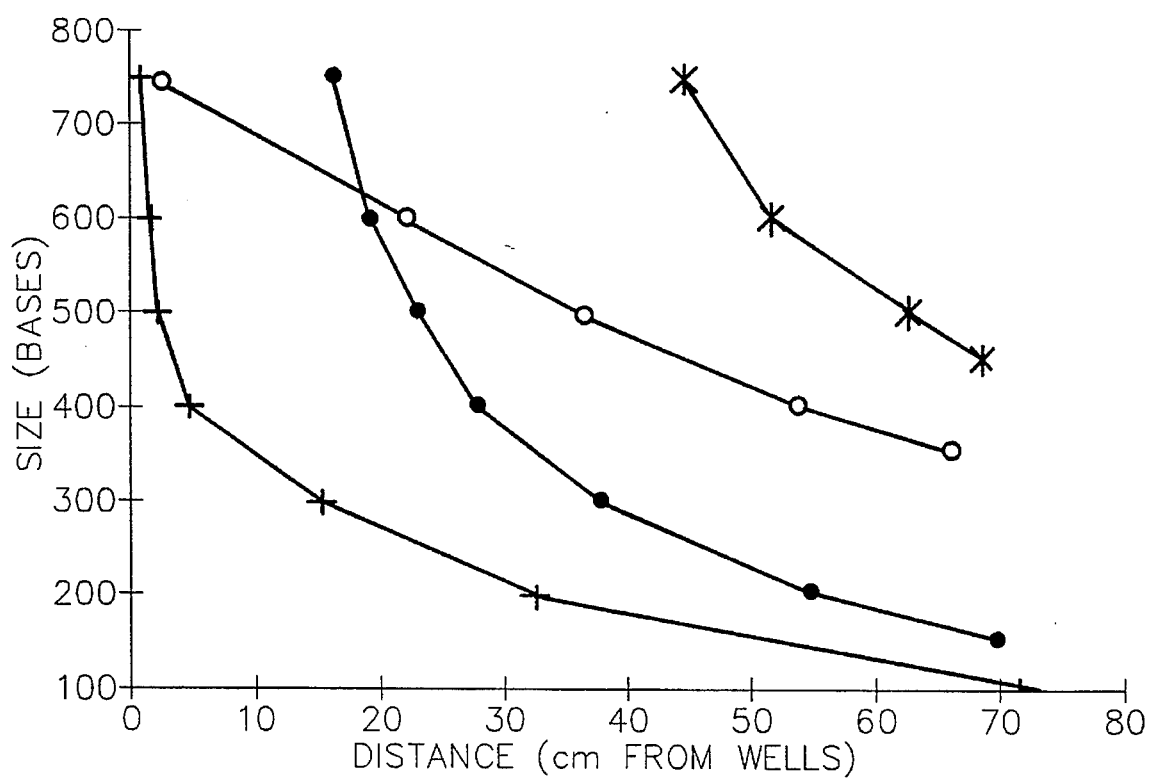
FIG. 5 is a computer simulation of the migration distances of single-stranded DNA molecules in conventional and MZPFGE gels using existing mobility data and the following assumptions: (1) In the conventional gel: gel length of 72 cm, 5% polyacrylamide gel, constant voltage gradient of 35 V/cm; (2) in the MZPFGE gel: distance between the samples and the interface is 2 cm; pulsed condition in Zone I is $E_+$=12.5 V/cm, $t_+$=1 s, $E_-$=35 V/cm, $t_-$=0.25 s; constant field strength of 35 V/cm in Zone II. Gel runs represented are: MZPFGE of 10 hours (plus signs); MZPFGE of 28 hours (open circles); conventional electrophoresis of 10 hours (closed circles); conventional electrophoresis of 28 hours (asterisks).

Another illustration of the MZPFGE technique in separation of SS DNA can be seen in FIG. 5, a graph comparing the calculated distances travelled by SS DNA molecules in MZPFGE gels (PFGE in Zone I and conventional electrophoresis in Zone II) and conventional electrophoresis gels, after 10 and 28 hour run durations. Both gels are 72 cm long. In the MZPFGE gel, the samples are placed 2 cm from the interface, and Zone II is 70 cm in length. After 28 hours, the resolution of the MZPFGE gel (slope of the line) from 600–750 bases is almost identical to that of the conventional gel at 150–250 bases. This is consistent with the above-stated conclusion that under these MZPFGE conditions, there is a minimum of a 3-fold increase in resolution over that obtained using conventional gels. Note the near-linearity of the MZPFGE curve at 28 hours. These curves are similar to the actual MZPFGE agarose DS DNA separations shown in FIG. 4. This indicates that the logarithmic dependence of SS DNA separation can be transformed into a linear function using MZPFGE. Single base separations up to 500–600 bases are possible in a conventional sequencing gel; the 3-fold increase in resolution calculated under these conditions indicates that single base separation up to at least 1.5–2 kb is obtainable using MZPFGE.

EXAMPLE 5

Gating at the Interface between Two Zones in a Vertical MZPFGE Apparatus

In two zone gel electrophoresis the interface between the two zones can be used as a "gate" to selectively release molecules from the first zone into the second zone. Molecules on one side of the interface experience field $E_I$; molecules on the other side experience field $E_{II}$. Through appropriate choice of $E_I$ and $E_{II}$, some molecules will be stopped at the interface whereas others, of different molecular weight M, will cross the interface into region II.

Experiments to Determine Suitable Pulse Protocols.

Before testing the vertical two-zone chamber, it was first necessary to determine the conditions ($t_+$, $t_-$, $E_+$, and $E_-$) that would give zero integrated velocity over one complete field cycle in a standard 1-zone chamber. These conditions are called ZIVE conditions. Under ZIVE conditions, a DNA band will have zero net displacement at the end of one complete cycle of the electrophoretic field.

ZIVE conditions were determined in a separate experiment carried out in a standard submarine electrophoresis chamber. A video camera, image-processing board, computer and computer program were used to record the position x of a band of fluorescently stained DNA in this chamber during electrophoresis. The electrophoretic field applied to the gel was controlled by the same computer program. The apparatus is described in Keiner and Holzwarth, *J. Chem. Phys.*, 97, 4476 (1992). To measure ZIVE conditions for the particular DNA in a gel, the computer program carried out the following sequence of steps:

a) measure initial band position $x^0$;

b) turn on the electrophoretic field to the desired $E_+$ and leave the field on for the selected time $t_+$;

c) change the electrophoretic field to the desired value $E_-$ and set time t of a timing function in the computer so that t=o;

d) measure new band position x and new time t; field $E_-$ remains on;

e) if $x-x^0>0$, repeat step d, recording a new value of x and a new value of t until $x-x^0 \leq 0$;

f) if $x-x^0 \leq 0$, store t as the ZIVE value of $t_-$;

g) repeat steps (a) to (f) for a new value of $E_+$, $E_-$, or $t_+$ to determine another value of $t_-$.

Figure 6A:
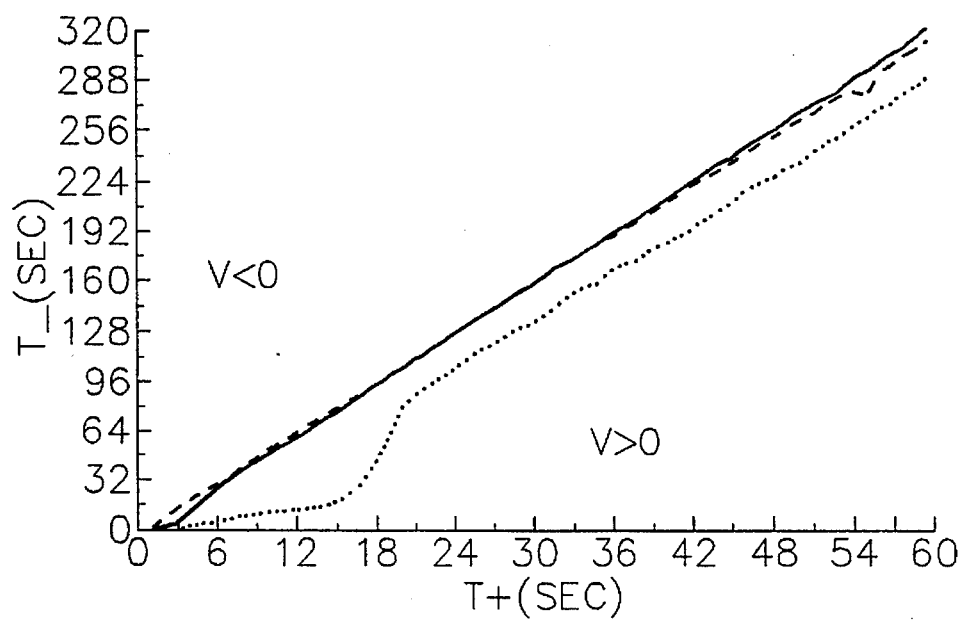
FIG. 6A is a graph showing zero integrated velocity electrophoresis (ZIVE) conditions for lambda DNA (dashed line), T4 DNA (solid line) and G DNA (dotted line), where $E_+$=12 V/cm, $E_-$=4 V/cm, and $t_-$ varies from 0 s to 320 s, and $t_+$ varies from 1 s to 60 s.
Figure 6B:
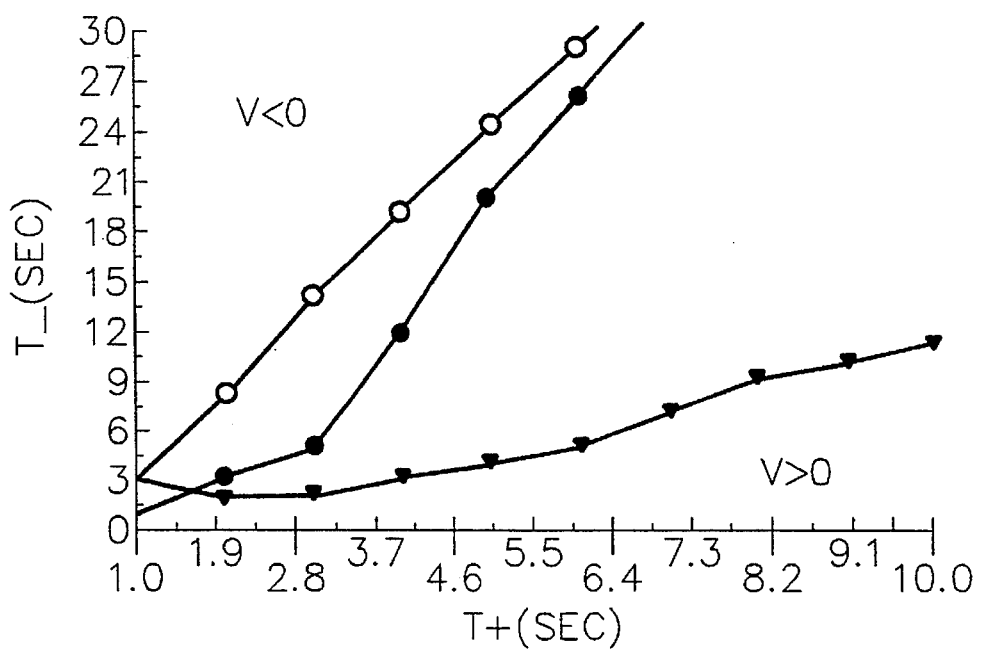
FIG. 6B is an expanded graph showing zero integrated velocity electrophoresis (ZIVE) conditions for lambda DNA (open circle), T4 DNA (closed circle), and G DNA (triangles), where $E_+$=12 V/cm, $E_-$=4 V/cm, $t_+$ varies from 1 s to 10 s, and $t_-$ varies from 1 s to 30 s.

ZIVE conditions for lambda DNA, T4 DNA, and G DNA are presented in FIG. 6A for $E_+=12$ V, $E_-=4$ V. FIG. 6B shows in greater detail the ZIVE conditions for $0<t_+<10$ s. A ZIVE curve for one type of DNA was measured using this method in several hours. Note that the ZIVE conditions are different for different M. For a given value of $t_+$, values of $t_-$ above the ZIVE line lead to a net negative velocity for that M. From the data in FIG. 6, electrophoretic conditions can be selected which lead to positive net velocity for one value of M but negative net velocity for a different M.

ZIVE conditions differ fundamentally from Slater, Turmel and Noolandi's zero-integrated-field-electrophoresis (ZIFE) conditions, for which $E_+t_+=E_-t_-$. See Turmel et al., in *Electrophoresis of Large DNA Molecules*, Birren and Lai (Eds.), Cold Spring Harbor Press, 101–132 (1990); Noolandi and Turmel, *Methods in Molecular Biology*, Vol. 12, 73 (1992); U.S. Pat. No. 5,167,784; U.S. Pat. No. 4,971,671. ZIVE conditions depend upon the size of the DNA. For example, the ZIVE data show that the velocity of T4 DNA is negative for all $t_- \geq 6$ s, whereas the average velocity of lambda DNA is negative only for $t_- \geq 18$ s.

While the present inventors do not wish to be bound to any mechanism of action, a qualitative molecular interpretation of these results can be made on the basis of measurements of the instantaneous velocity of linear DNA after field inversion (Platt and Holzwarth, *Phys. Rev. A*, 40, 7292, 1989), video micrographs of DNA during gel electrophoresis (Smith et al., *Science* 243, 203, 1989), and computer simulations of the motions of DNA during electrophoresis in gels (Deutsch and Madden *J. Chem. Phys.*, 90, 2478, 1991; Zimm, *J. Chem. Phys.* 94, 2187 1991). The velocity measurements show that immediately after field inversion, there is a rapid recoil of the molecular center of mass. The magnitude (distance) of this recoil is larger for larger DNA molecules, but requires that the preceding "setup" pulse be long enough for the DNA to become stretched out. After the rapid recoil, there is a shallow minimum in velocity before the steady-state velocity is reached. The time to reach this steady-state velocity is longer for larger chains. Because of the recoil, larger molecules have a larger negative velocity during the reverse pulse than do smaller molecules. In addition, during the forward pulse the larger molecules do not recoil as much if the reverse pulse was too short to set them up for a recoil, but the same pulse duration may be long enough to set up the smaller chains for their recoil. The net velocity for a given M is thus a complicated function of $t_+$, $t_-$, $E_+$, and $E_-$.

Results with Vertical Two Zone Chamber.

Figure 7A:
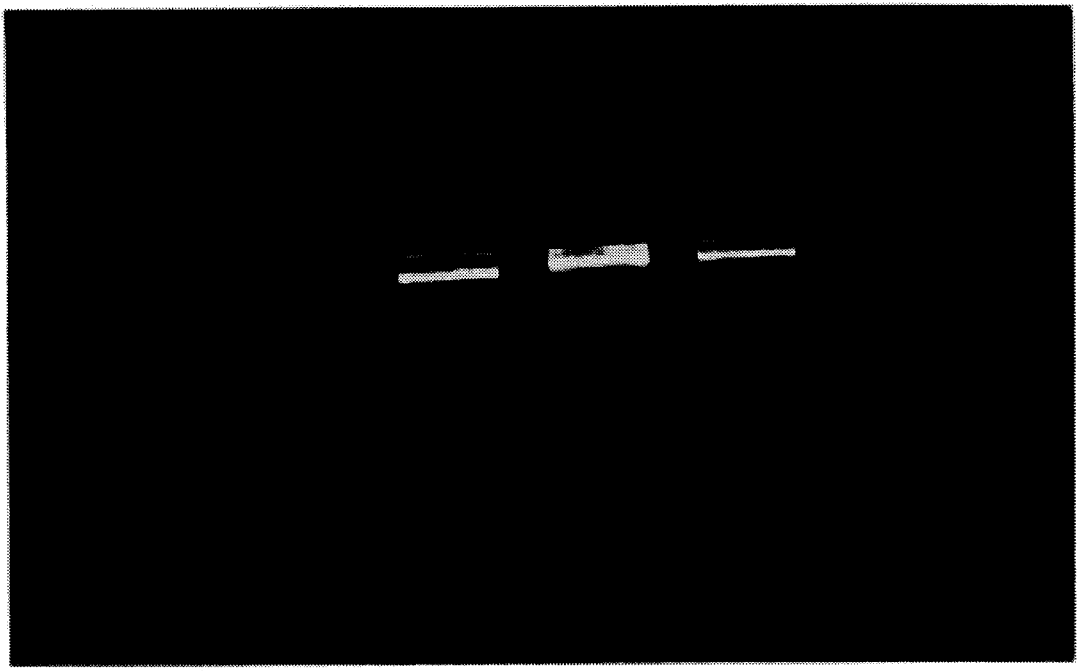
FIG. 7A is a photograph of a vertical electrophoresis gel containing samples of T4 DNA (Lane 1), a mixture of T4 DNA and G DNA (Lane 2) and G DNA (Lane 3) after 45 minutes of a constant field of 4 V/cm.
Figure 7B:
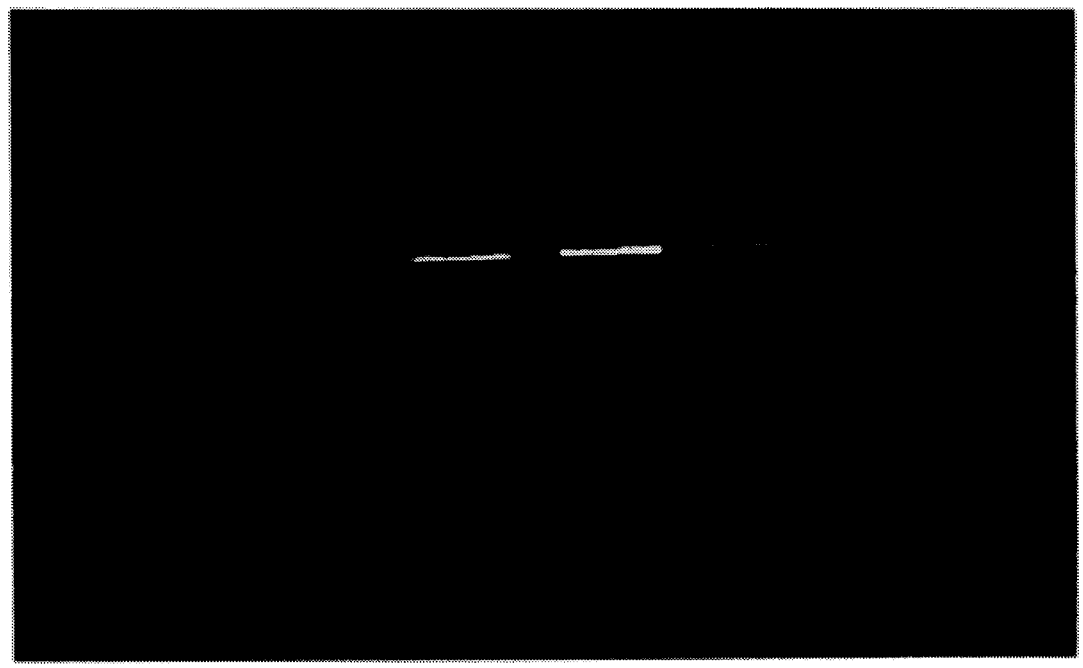
FIG. 7B is a photograph of the gel of FIG. 7A, after undergoing 45 minutes of a constant field of 12 V/cm.
Figure 7C:
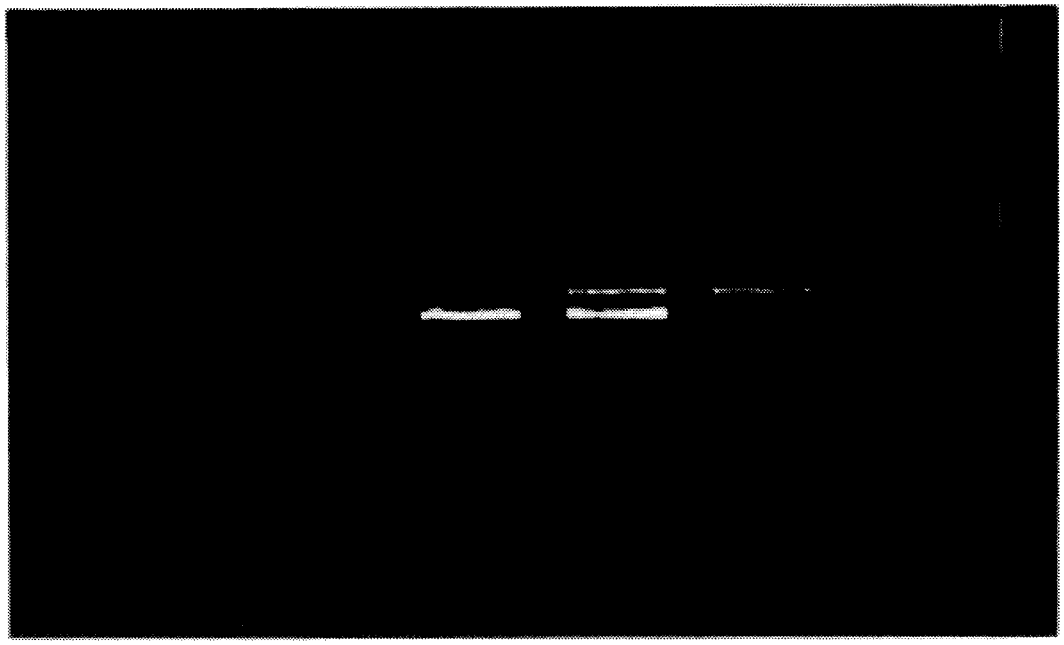
FIG. 7C is a photograph of the gel of FIG. 7B, after undergoing 30 minutes of MZPFGE, where $E_I$ was $E_+$=4 V/cm, $t_+$=10 s, $E_-$=0, $t_-$=20 s; and $E_{II}$ was $E_+$=12 V/cm, $t_+$=10 s, $E_-$=4 V/cm, $t_-$=20 s (these parameters set $E_I$=0 whenever $E_{II}$ was negative).
Figure 7D:
FIG. 7D is a photograph of the gel of FIG. 7C, after undergoing an additional 30 minutes of MZPFGE where $E_I$ was $E_+$=4 V/cm, $t_+$=10 s $E_-$=0, $t_-$=20 s; and $E_{II}$ was $E_+$=12 V/cm, $t_+$=10 s, $E_-$=4 V/cm, $t_-$=20 s (which set $E_I$=0 whenever $E_{II}$ was negative).
Figure 7E:
FIG. 7E is a photograph of the gel of FIG. 7D, after undergoing 30 minutes of MZPFGE where $E_I$ was $E_+$= 4 V/cm, $t_+$=10 s, $E_-$=0, $t_{31}$=8 s; and $E_{II}$ was $E_+$=12 V/cm, $t_+$=10 s, $E_-$=4 V/cm, $t_-$=8 s (which set $E_I$=0 whenever $E_{II}$ was negative).
Figure 8A:
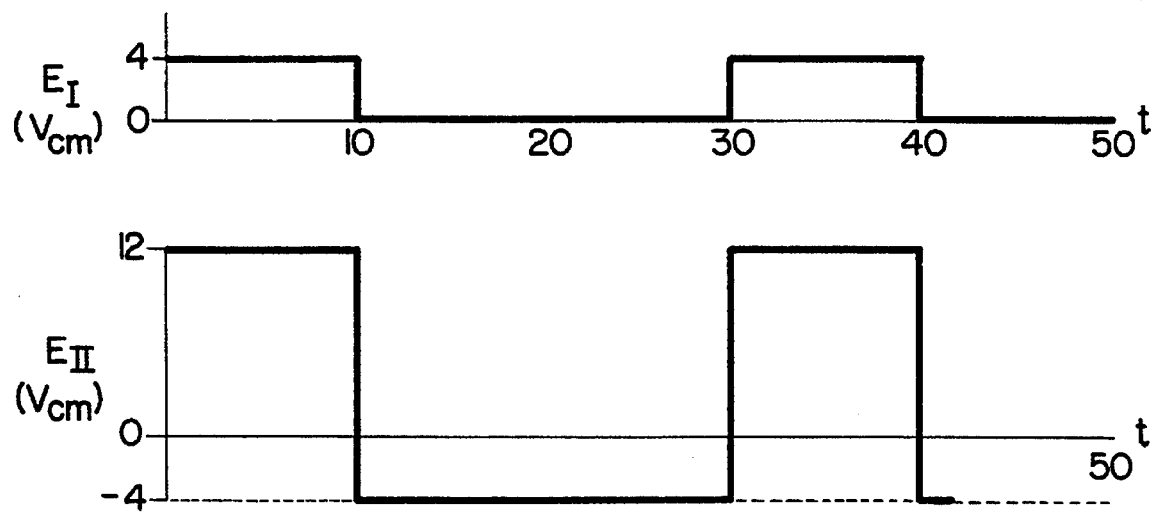
FIG. 8A is a schematic of the electric fields applied in Zone I ($E_I$) and Zone II ($E_{II}$) during the electrophoretic separation of FIG. 7C; where $E_I$ was $E_+$= 4 V/cm, $t_+$=1 s, $E_-$=0, $t_-$=20 s; and $E_{II}$ was $E_+$=12 V/cm, $t_+$ =10 s, $E_-$=4 V/cm, $t_-$=20 s (which set $E_I$=0 whenever $E_{II}$ was negative).
Figure 8B:
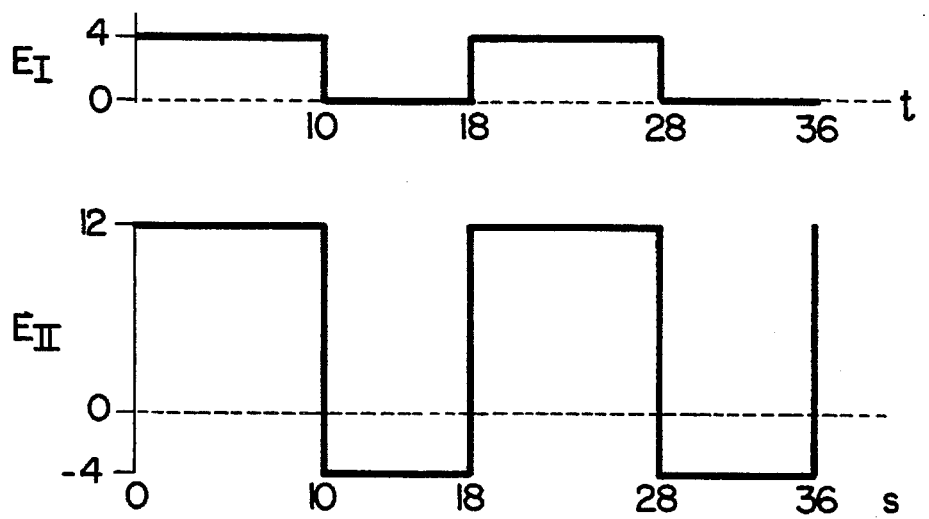
FIG. 8B is a schematic of the electric fields applied in Zone I ($E_I$) and Zone II ($E_{II}$) during the electrophoretic separation of FIG. 7E; where $E_I$ was $E_+$= 4 V/cm, $t_+$=10 s, $E_-$=0, $t_-$=8 s; and $E_{II}$ was $E_+$=12 V/cm, $t_+$=10 s, $E_-$=4 V/cm, $t_-$=8 s (which set $E_I$=0 whenever $E_{II}$ was negative).

A 1% agarose gel with three sample wells was prepared for a vertical gel apparatus (as diagrammed in FIG. 3) and the three wells were loaded with DNA samples. Lane 1 contained T4 DNA; Lane 2 contained a mixture of T4 DNA and G DNA; Lane 3 contained only G DNA. The experiment was run in several stages; photographs of the gels are shown in FIG. 7A–E. In stage 1, the "gel-entry prerun", fields with $E_I=4$ V/cm and $E_{II}=0$ were applied for 45 min to ease the DNA into the gel (FIG. 7A). The DNAs were then all moved to the interface with $E_I=12$ V/cm and $E_{II}=0$ for 45 min (FIG. 7B). Note that both T4 DNA and G DNA stopped at the interface between regions I and II. For the next period, $E_{II}$ was set to $E_+=12$ V/cm, $t_+=10$ s, $E_-=4$ V/cm, $t=20$ s; these conditions were chosen such that the velocity of T4 DNA was positive while that of G DNA was negative (see FIG. 6). In addition, $E_I$ was set to the pattern shown in FIG. 8A ($E_+=4$ V/cm, $t_+=10$ s; $E_-=0$, $t_-=20$ s), which set $E_I=0$ whenever $E_{II}$ was negative. If this was not done, the bands tended to disappear at the interface, presumably because the field had a component perpendicular to the face of the gel which pushed the DNA out of the gel. After 30 min, the T4 DNA had moved about 2.2 mm past the interface while the G DNA remained stationary at the interface "gate" (FIG. 7C). An additional 30 minutes of this procedure moved the T4 DNA about 4.5 mm past the interface but still the G DNA remained in place at the interface (FIG. 7D). Finally, new conditions were selected, based on the data shown in FIG. 6, to allow the G DNA to advance past the gate. Specifically, $t_-$ was changed to 8 s while leaving all other parameters unaltered (FIG. 8B). After 1 h of this pulse protocol, the G DNA had moved about 4 mm past the interface, while T4 DNA moved even further away (FIG. 7E). This showed that the interface between two regions of a gel could be used as a molecular gate by appropriate choice of fields in the two regions.

A problem in conventional, single zone PFGE and FIGE is band inversion. See Carle et al., *Science*, 232, 65 (1986). Inspection of FIG. 6B shows that this could also occur in the gating procedure of MZPFGE as well, since the ZIVE conditions for different sizes of DNA cross one another at short pulse durations. However, the data given in FIG. 6A and 6B show that a sequence of values of $t_+$ and $t_-$ can be selected which will avoid band inversion, i.e., which will allow progressively larger molecules to be released by the gate. For example, a progression beginning at ($t_+=1.0$ s; $t_-=12$ s) and ending at ($t_+=7.3$ s; $t_-=1.0$ s) would release lambda DNA, T4 DNA, and G DNA in sequence. Changes in field can also be used to avoid band inversion.

The foregoing examples are illustrative of the present invention, and are not to be construed as limiting thereof. The invention is defined by the following claims, with equivalents of the claims to be included therein.

That which is claimed is:

1. A method for gel electrophoresis, comprising:

positioning a sample of molecules to be electrophoretically separated in an electrophoresis gel medium; and applying two electric fields to said gel to provide a first zone and a second zone, said first and second zones having different electric field values and existing simultaneously in said gel, wherein an asymmetric voltage field-inversion electric field is applied to one of said zones.

2. A method according to claim 1, wherein said sample is positioned at the interface of said first zone and said second zone.

3. A method according to claim 2, wherein an asymmetric voltage field-inversion electric field is applied to said first zone, and a constant electric field is applied to said second zone.

4. A method according to claim 3, wherein values of the electric field in said first zone are selected to release molecules of a pre-selected size from said first zone into said second zone.

5. A method according to claim 3, wherein values of the electric field in said first zone are selected to release molecules of progressively larger sizes from said first zone into said second zone.

6. A method according to claim 2, wherein an asymmetric voltage field-inversion electric field is applied to said first zone, and a pulsed electric field is applied to said second zone.

7. A method according to claim 6, wherein values of said electric field of said first zone are selected to release molecules of a preselected size from said first zone into said second zone.

8. A method for gel electrophoresis, comprising:

applying two electric fields to an electrophoretic gel medium so that two separate zones having different electric field values exist simultaneously in said gel; and positioning a sample of molecules to be electrophoretically separated in said gel medium at the interface of said first zone and said second zone;

wherein an asymmetric voltage field-inversion electric field is applied to each of said two zones, and wherein the electric field of said first zone is equal to zero whenever the electric field of said second zone is negative.

9. A method according to claim 8, wherein values of the electric fields in said two zones are selected to retain molecules above a preselected size in said first zone.

* * * * *